US008930386B2

(12) United States Patent
Mayr et al.

(10) Patent No.: US 8,930,386 B2
(45) Date of Patent: *Jan. 6, 2015

(54) QUERYING BY SEMANTICALLY EQUIVALENT CONCEPTS IN AN ELECTRONIC DATA RECORD SYSTEM

(75) Inventors: Florian Alexander Mayr, Mountain View, CA (US); Anand Shroff, San Carlos, CA (US); Hamish Daniel Currie, Red Hill (AU); Gregory Kuhnen, Evanston, IL (US); Matthew Thomas Moores, Ferny Grove (AU)

(73) Assignee: Oracle International Corporation, Redwood Shores, CA (US)

( * ) Notice: Subject to any disclaimer, the term of this patent is extended or adjusted under 35 U.S.C. 154(b) by 746 days.

This patent is subject to a terminal disclaimer.

(21) Appl. No.: 12/485,888

(22) Filed: Jun. 16, 2009

(65) Prior Publication Data

US 2010/0318549 A1    Dec. 16, 2010

(51) Int. Cl.
  *G06F 7/00*    (2006.01)
  *G06F 17/30*    (2006.01)
  *G06F 19/00*    (2011.01)

(52) U.S. Cl.
  CPC .................................. *G06F 19/322* (2013.01)
  USPC .......................................... 707/759; 707/765

(58) Field of Classification Search
  CPC .................... G06F 17/30731; G06F 17/30734; G06F 17/30592; G06F 17/30672; G06F 17/30616; G06F 17/30598; G06F 17/30637; G06F 17/3043; G06F 17/30643; G06F 19/322; G06F 15/16; G06F 12/00; G06Q 10/10; G06Q 30/02; Y10S 707/956; Y10S 707/9942; Y10S 707/9943; Y10S 707/99944; Y10S 707/99945
  See application file for complete search history.

(56) References Cited

U.S. PATENT DOCUMENTS

| 5,063,507 | A | * | 11/1991 | Lindsey et al. | 705/37 |
| 5,285,383 | A | * | 2/1994 | Lindsey et al. | 705/37 |
| 5,794,236 | A | * | 8/1998 | Mehrle | 1/1 |
| 6,327,593 | B1 | * | 12/2001 | Goiffon | 1/1 |
| 6,438,560 | B1 | * | 8/2002 | Loen | 707/803 |
| 6,453,312 | B1 | * | 9/2002 | Goiffon et al. | 1/1 |
| 7,007,018 | B1 | * | 2/2006 | Kirkwood et al. | 707/694 |
| 7,194,483 | B1 | * | 3/2007 | Mohan et al. | 707/600 |

(Continued)

OTHER PUBLICATIONS

Medical Education Taxonomy Research Organization (METRO) First Phase Project Report, Ellaway et al.; METRO Project Report—Aug. 2003.*

(Continued)

*Primary Examiner* — Daniel Kuddus
(74) *Attorney, Agent, or Firm* — Meyer IP Law Group

(57) ABSTRACT

Embodiments of the present invention enable processing of concept-based query requests submitted to a query service within a healthcare transaction framework. In embodiments, a terminology service within the healthcare transaction framework manages terminology content (concepts represented by a set of terminologies). In embodiments, search criteria from a data access query request are submitted to the terminology service to extract a set of concepts from the terminology content that are associated with the search criteria. In embodiments, equivalence search criteria include a seed concept, and the terminology service returns a set of equivalent concepts comprising the seed concept. In embodiments, classification search criteria include a classification identifier, and the terminology service returns a set of concepts associated with the classification identifier. In embodiments, the query service generates and submits a data access query comprising predicates associated with the returned set of concepts.

19 Claims, 12 Drawing Sheets

(56) References Cited

U.S. PATENT DOCUMENTS

| | | | |
|---|---|---|---|
| 7,644,052 B1* | 1/2010 | Chang et al. | 706/45 |
| 8,407,197 B2 | 3/2013 | Zasman et al. | |
| 8,428,367 B2 | 4/2013 | Ahmed | |
| 8,463,810 B1 | 6/2013 | Rennison | |
| 8,484,691 B2 | 7/2013 | Schmelzer | |
| 8,504,564 B2 | 8/2013 | Chang et al. | |
| 8,543,998 B2 | 9/2013 | Barringer | |
| 8,589,311 B2 | 11/2013 | Bhatt et al. | |
| 8,601,062 B2 | 12/2013 | Buchheit et al. | |
| 2003/0217052 A1* | 11/2003 | Rubenczyk et al. | 707/3 |
| 2005/0203924 A1* | 9/2005 | Rosenberg | 707/100 |
| 2005/0240583 A1* | 10/2005 | Li et al. | 707/7 |
| 2006/0167930 A1* | 7/2006 | Witwer et al. | 707/102 |
| 2007/0198506 A1* | 8/2007 | Attaran Rezaei et al. | 707/5 |
| 2008/0281915 A1* | 11/2008 | Elad et al. | 709/204 |
| 2009/0222400 A1 | 9/2009 | Kupershmidt et al. | |
| 2009/0299857 A1* | 12/2009 | Brubaker | 705/14.66 |
| 2009/0313217 A1* | 12/2009 | Signorini et al. | 707/3 |
| 2010/0318548 A1* | 12/2010 | Mayr et al. | 707/759 |

OTHER PUBLICATIONS

Goble et al., Transparent Access to Multiple Bioinformatics Information Sources, IBM Systems Journal, vol. 40, No. 2, 2001, pp. 532-551, 20 pages.

* cited by examiner

Intra-Version Equivalence

| Custom Coding Scheme |
|---|
| 26702 - Breathless |
| ↕  — 600a |
| 26703 - Breathlessness |
| ↕  — 600b |
| 26704 - Dyspnea |
| ↕  — 600c |
| 26705 - SOB - Shortness of breath |

FIGURE 6

Inter-Version Equivalence

| Concept Code – v 1.0 | Concept Code – v 2.0 | Concept Description |
|---|---|---|
| 26702 | | Breathless |
| 26703 | 26703 | Breathlessness |
| 26704 | 26704 | Dyspnea |
| 26705 | 26705 | SOB – Shortness of breath |
| | | |

700

QUERYING BY SEMANTICALLY EQUIVALENT CONCEPTS IN AN ELECTRONIC DATA RECORD SYSTEM

CROSS REFERENCE TO RELATED PATENT APPLICATIONS

This application is related to U.S. patent application Ser. No. 12/485,876, filed Jun. 16, 2009, entitled QUERYING BY CONCEPT CLASSIFICATIONS IN AN ELECTRONIC DATA RECORD SYSTEM, by Mayr, et al. The above-referenced application is incorporated herein by reference in its entirety.

BACKGROUND

A. Technical Field

The present invention pertains generally to data processing, and relates more particularly to querying in an electronic data record system.

B. Background of the Invention

Healthcare is one industry for which viewing and sharing of information are vitally important. For instance, in order to provide effective healthcare to a patient, it is essential to be able to access a trusted persistent record of that patient's medical history. However, the unification of information stored within disparate data repositories presents a difficult problem. Until recently, it has been almost impossible for different healthcare organizations and service providers to be able to view a trusted common electronic record of a person's medical history discordant terminologies with poorly developed mechanisms for sharing the data between disparate systems. This had led to access and interoperability obstacles that prevent the presentation of an integrated view of a single patient's data.

The Health Level 7 Version 3 (HL7 v3) international standard has been developed to remove some of the interoperability obstacles by providing a platform for data consolidation. HL7 v3 includes a Reference Information Model (RIM) that enforces consistency of stored and shared information across diverse domains within healthcare. HL7 v3 and RIM facilitate the collection of patient and healthcare data from disparate systems, as well as the storage of that data in a central repository without losing its meaning so that it can be shared electronically via a secure connection across different systems in diverse organizations. The HL7 v3 standard also supports a concept-based semantics terminology model to support multiple representations of healthcare concepts in the various terminologies used within the industry. Additionally, HL7 v3 specifies methods for binding terminologies to RIM structural concepts so that a standard common semantics model for data describing healthcare concepts may be developed.

One approach to removing some of the data access obstacles is to provide a healthcare information exchange platform that combines a standards-based central data repository (such as an HL7 v3 compliant central data repository) with an integrated set of services for managing and accessing the data in the central repository. The healthcare information exchange platform typically includes a query service that provides programmatic interfaces for accessing the data stored in the data repository. To enable efficient querying of the data, it would be useful to develop a robust searching mechanism that can leverage concept-based semantics, such as the semantics model specified by HL7 v3.

SUMMARY OF THE INVENTION

Embodiments of the present invention enable processing of concept-based query requests submitted to a query service within a healthcare transaction framework. In embodiments, a terminology service within the healthcare transaction framework manages terminology content (concepts represented by a set of terminologies). In embodiments, search criteria from a data access query request are submitted to the terminology service to extract a set of concepts from the terminology content that are associated with the search criteria. In embodiments, equivalence search criteria include a seed concept, and the terminology service returns a set of equivalent concepts comprising the seed concept. In embodiments, classification search criteria include a classification identifier, and the terminology service returns a set of concepts associated with the classification identifier. In embodiments, the query service generates and submits a data access query comprising predicates associated with the returned set of concepts.

In embodiments, generating a query to retrieve a set of stored data records from an electronic data record system may comprise receiving a query request comprising a set of search criteria comprising a seed concept; generating an equivalence concept query based on at least a subset of the search criteria that includes the seed concept; receiving a set of concepts that are semantically equivalent to the seed concept in response to submitting the equivalence concept query to a terminology service that manages a repository of terminology content; and generating the query comprising predicates corresponding to the seed concept and the set of concepts that are semantically equivalent to the seed concept.

In embodiments, the terminology content comprises concepts that are associated with at least one terminology code system and, in embodiments, the seed concept has a coded data type. In embodiments, the subset of search criteria comprises an equivalence definition type and, in embodiments, the equivalence definition type is semantic equivalence or mapping equivalence. In embodiments, the subset of search criteria comprises an indication of an equivalence definition domain boundary and, in embodiments, the equivalence definition domain boundary is indicated to be within a single code system associated with a terminology or is indicated to span across a plurality of code systems associated with a plurality of terminologies. In embodiments, the equivalence definition domain boundary is indicated to be within a usage context.

In embodiments, a system to generate a database query to retrieve a set of stored data records from an electronic data record system may comprise a concept query system, coupled to receive a concept query request comprising a set of search criteria that comprises a seed concept, that generates a concept query result in response to submitting an equivalence concept query to a terminology service that manages a repository of terminology content comprising mappings between the stored concepts; and a database query generator, coupled to receive the concept query result comprising the seed concept and a retrieved set of concepts that are semantically equivalent to the seed concept, that generates the database query comprising predicates associated with the seed concept and the retrieved set of concepts that are semantically equivalent to the seed concept.

In embodiments, the system further comprises a database query processor, coupled to receive the database query, that retrieves the set of stored data records in response to submitting the database query to the electronic data record system.

In embodiments, the concept query system may comprise a concept query generator, coupled to receive the set of search criteria that comprises the seed concept, that generates the equivalence concept query comprising the seed concept; and a concept query results generator, coupled to receive the equivalence concept query, that generates the concept query result in response to submitting the equivalence concept query to the terminology service.

In embodiments, a method for generating a set of semantically equivalent concepts may comprise receiving a set of search criteria comprising a seed concept; retrieving a set of stored concepts that are semantically equivalent to the seed concept from a terminology content data repository; and generating the set of semantically equivalent concepts comprising the seed concept and the retrieved set of semantically equivalent concepts.

In embodiments, the set of semantically equivalent concepts have inter-version semantic equivalence. In embodiments, the set of semantically equivalent concepts are associated with a plurality of terminology codes and have inter-terminology mapping equivalence.

In embodiments, generating a query to retrieve a set of stored data records from an electronic data record system may comprise receiving a query request comprising a set of search criteria comprising a classification identifier; generating a classification concept query based on at least a subset of the search criteria that includes the classification identifier; receiving a set of stored concepts that are associated with the classification identifier in response to submitting the classification concept query to a terminology service that manages a repository of terminology content comprising stored concept containers having corresponding classification identifiers; and generating the query comprising predicates corresponding to the set of stored concepts.

In embodiments, the set of stored concepts associated with the classification identifier have an IS-A relationship with a concept container associated with the classification identifier. In embodiments, a classification hierarchy comprises a first concept container and a set of concept containers having an IS-A relationship to the first concept container.

In embodiments, the terminology content comprises stored concepts that are associated with at least one terminology and, in embodiments, the subset of search criteria comprises at least one attribute having a coded data type. In embodiments, a concept container is associated with a set of attributes described in part by at least one terminology code, and a concept within the set of stored concepts is identified based in part on a terminology code.

In embodiments, a system to generate a database query to retrieve a set of stored data records from an electronic data record system may comprise a concept query system, coupled to receive a concept query request comprising a set of search criteria that comprises a classification identifier, that generates a concept query result in response to submitting a classification concept query to a terminology service that manages a repository of terminology content comprising stored concept containers having corresponding classification identifiers; and a database query generator, coupled to receive the concept query result, that generates the database query comprising predicates associated with the retrieved set of stored concepts.

In embodiments, the system further comprises a database query processor, coupled to receive the database query, that retrieves the set of stored data records in response to submitting the database query to the electronic data record system. In embodiments, the system further comprises a database query service API that receives the concept query request and returns a database query result comprising the retrieved set of stored data records.

In embodiments, the concept query system may comprise a concept query generator, coupled to receive the set of search criteria that comprises the classification identifier, that generates the classification concept query comprising the classification identifier; and a concept query results generator, coupled to receive the classification concept query, that generates the concept query result in response to submitting the classification concept query to the terminology service.

In embodiments, a method for generating a set of stored concepts that are associated with a classification may comprise receiving a set of search criteria comprising a classification identifier; identifying a classification concept container that is associated with the classification identifier (the classification concept container being stored within a terminology content data repository); and generating the set of stored concepts by retrieving, from the terminology content data repository, concepts that have an IS-A relationship to the stored classification concept container.

In embodiments, a classification hierarchy comprises a first concept container and a set of concept containers having an IS-A relationship to the first concept container, and the classification identifier is associated with one of the stored classification concept containers within the classification hierarchy. In embodiments, containment of a stored concept within any one of the classification concept containers within the classification hierarchy may be determined in response to receiving the set of search criteria.

Some features and advantages of the invention have been generally described in this summary section; however, additional features, advantages, and embodiments are presented herein or will be apparent to one of ordinary skill in the art in view of the drawings, specification, and claims hereof. Accordingly, it should be understood that the scope of the invention shall not be limited by the particular embodiments disclosed in this summary section.

BRIEF DESCRIPTION OF THE DRAWINGS

Reference will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIG. 6 illustrates an exemplary intra-version equivalence definition according to various embodiments of the invention.

DETAILED DESCRIPTION OF THE PREFERRED EMBODIMENTS

Figure 1:
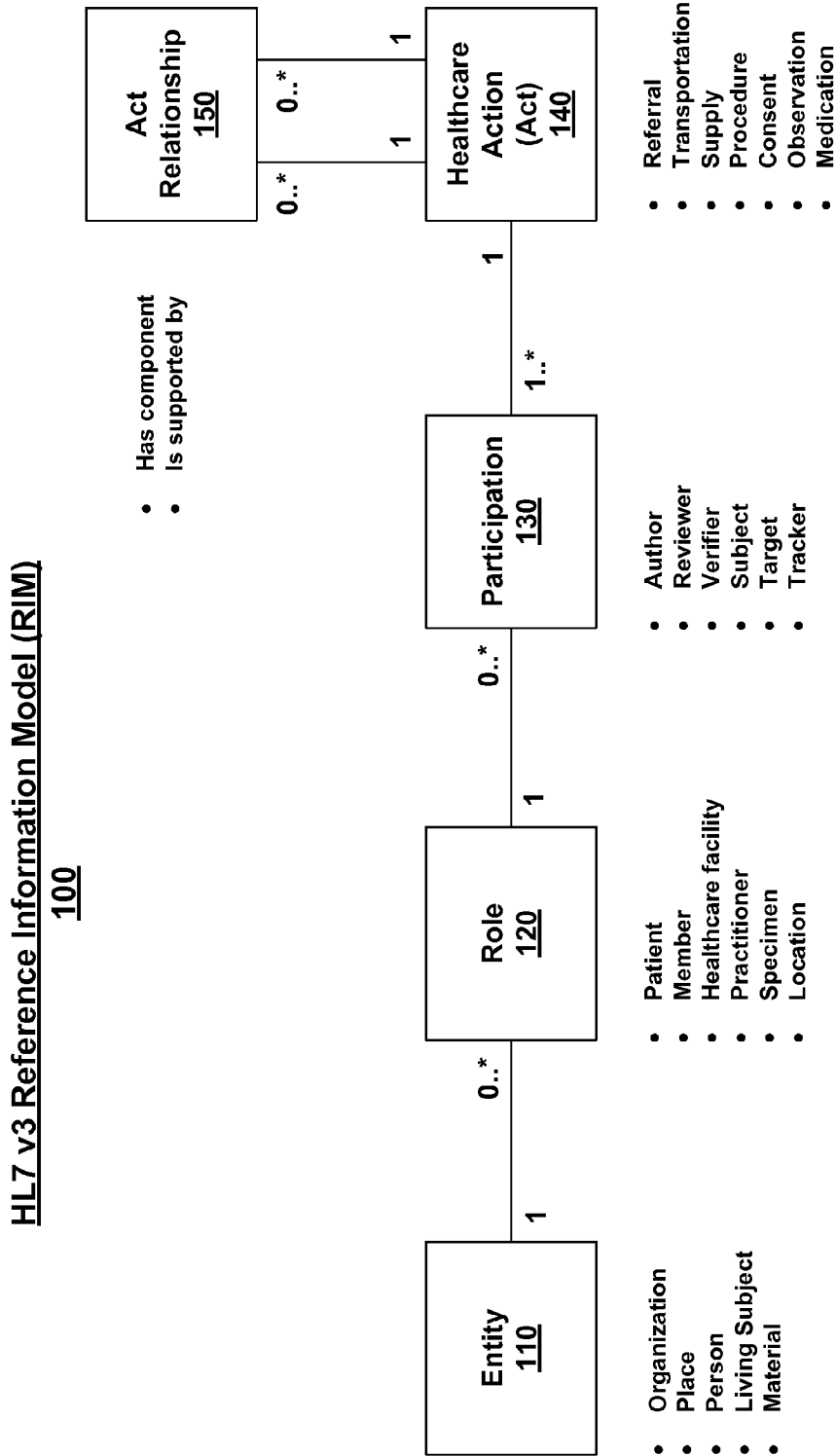
FIG. 1 is an illustration of the five abstract structural concepts (classes) comprising the HL7 v3 RIM.

In the following description, for purposes of explanation, specific details are set forth in order to provide an understanding of the invention. It will be apparent, however, to one skilled in the art that the invention can be practiced without these details. Furthermore, one skilled in the art will recognize that embodiments of the present invention, described below, may be implemented in a variety of ways, including software, hardware, or firmware, or combinations thereof. Accordingly, the figures described herein are illustrative of specific embodiments of the invention and are meant to avoid obscuring the invention.

Components, or modules, shown in block diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component.

Furthermore, connections between components within the figures are not intended to be limited to direct connections. Rather, data between these components may be modified, re-formatted, or otherwise changed by intermediary components. Also, additional or fewer connections may be used. It shall also be noted that the terms "coupled" or "communicatively coupled" shall be understood to include direct connections, indirect connections through one or more intermediary devices, and wireless connections.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. The appearances of the phrases "in one embodiment," "in an embodiment," or "in embodiments" in various places in the specification are not necessarily all referring to the same embodiment or embodiments.

The use of certain terms in various places in the specification is for illustration and should not be construed as limiting. Usage of the term "service" is not limited to describing a single function; usage of the term also may refer to a grouping of related functions or functionality. Similarly, usage of the term "resource" is not limited to describing a single resource; the term also may be used to refer to a set of resources that may either be distributed or aggregated within a computing environment.

A. Overview

One specific application of the present invention is its use in embodiments of a healthcare electronic data record computing system. These embodiments will be described for illustrative purposes and not for limitation. One skilled in the art will recognize the general applicability of the present invention to other data records.

1. The HL7 v3 Standard

The Health Level 7 Version 3 (HL7 v3) international standard allows information systems to share health information unambiguously by enabling semantic interoperability of data. Semantic interoperability of data refers to sharing meaning of data rather than just the structure of data. The HL7 v3 standard is comprised of four primary components: a common information model; a data type specification; a methodology for binding to concept-based terminologies; and a messaging model.

The HL7 v3 common information model is the Reference Information Model (RIM). The RIM provides a high-level backbone that defines the semantics of a set of common clinical, administrative, and financial data structures. FIG. 1 is an illustration of the five core abstract structural concepts (backbone classes) comprising the HL7 v3 RIM 100 along with exemplary implementations of each abstract class: Entity 110, representing things in the world; Role 120, representing capability, capacity, or competency (usually time-based); Participation 130, representing Role in the context of an Act; Act 140, representing clinical, administrative, or financial definitions, plans, and occurrences; and Act Relationship 150, representing the semantics of links between Acts.

RIM backbone classes may be associated with other types of RIM backbone classes to form data structures that represent higher level healthcare concepts. As depicted in FIG. 1, an Entity 110 may be associated with zero-to-many Roles 120; a Role 120 may be associated with zero-to-many Participations 130; one-or-many Participations 130 may be associated with one Act 140; and one Act 140 may be associated with zero-to-many of each type of Act Relationship 150.

Figure 2:
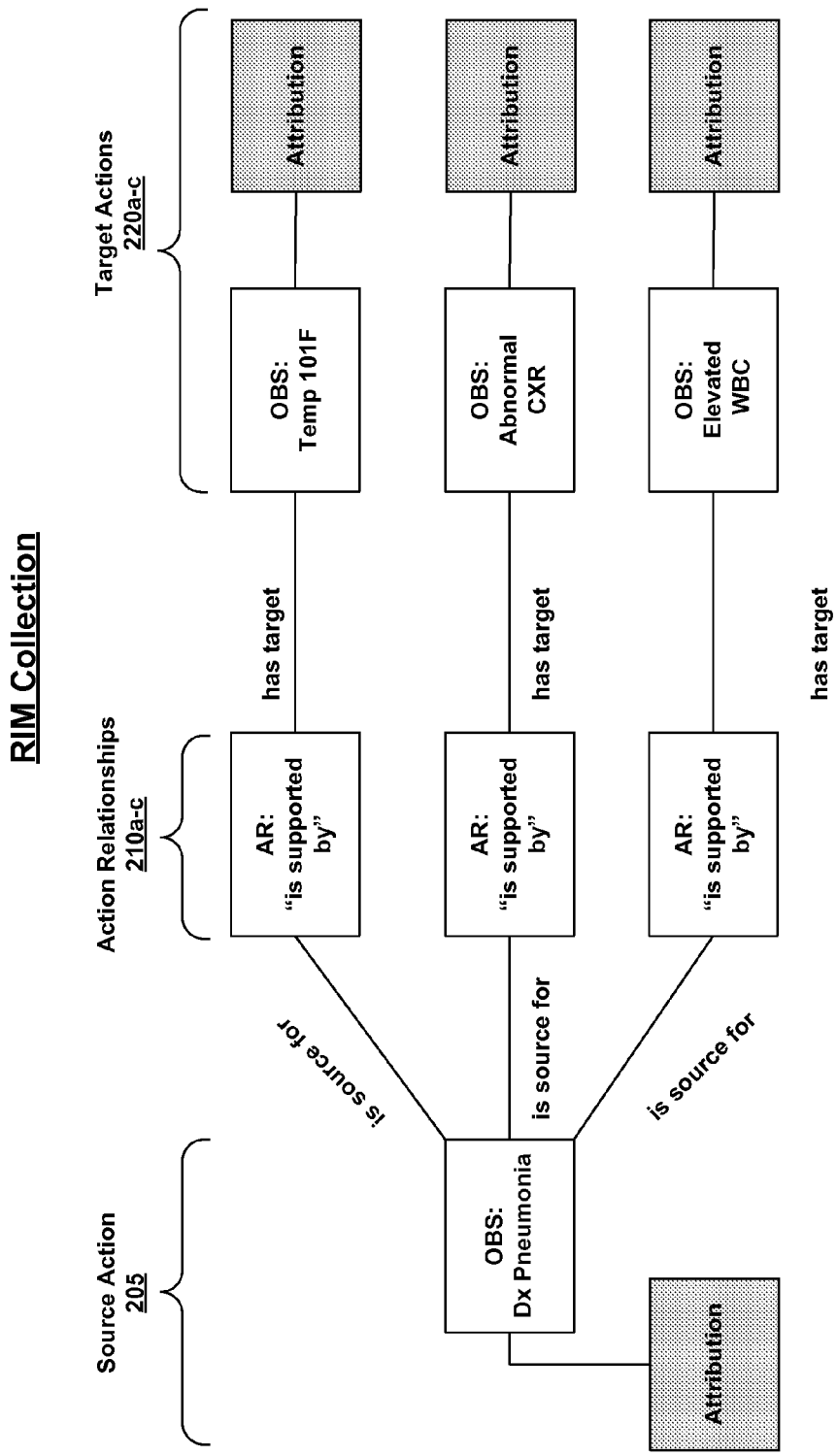
FIG. 2 is an illustration of an exemplary "collection" RIM data structure.

RIM backbone classes may have any number of sub-classes, each of which is defined by a set of additional associated attributes that specify its semantics. FIG. 2 depicts an exemplary "collection" RIM data structure representing a diagnosis of pneumonia (observation Act 205) related to three other observation Acts 220a-c. The Act Relationship classes 210a-c relating the source Act 205 to three target Acts 220a-c are used to capture the notion of a diagnosis as an observation about observations. In the example, each observation Act (205 and 220a-c) is associated with a set of attributes (attribution) describing its own context of Entity-Role-Participation values.

The semantics of an attribute are specified through its binding to an HL7 v3 data type. As is well known to those skilled in the art, a data type is used to represent the semantics (meaning) associated with a piece of data as well as the kinds of operations that may be performed using the piece of data. A data type may be a simple (atomic) data type (e.g., integer, floating point, character, and string), or it may be a complex data type (e.g., date, time, and address). HL7 v3 specifies a set of simple and complex data types that represent healthcare concepts (e.g., data types representing physical quantity, time intervals, and events).

The HL7 v3 data type specification includes a set of concept descriptor (coded) data types. A coded data type may be used to represent any kind of concept, usually by giving a code defined in a code system associated with a particular vocabulary domain ("terminology"). The semantics of a coded data type may be expanded or modified by its binding to a particular code or data value associated with a terminology. A terminology may be a healthcare industry-standard terminology (e.g., SNOMED-CT, LOINC, ICD-9, and CPT), an HL7 standard code set, or a custom terminology that is defined by a particular healthcare institution. A coded data type can contain a set of features which may include, for example, the original text or phrase that served as the basis of the coding, and one or more translations into different coding systems. HL7 v3 coded data types and their associated meanings are summarized in Table 1.

TABLE 1

HL7 v3 coded data types and their associated meanings

| HL7 Coded Data Type | Meaning |
|---|---|
| CD | Concept Descriptor - Basic coded data type that may contain all features including coding exceptions, text, translations, and qualifiers. |
| CS | Coded Simple Value - Coded data in its simplest form, where only the code is not predetermined. The code system and code system version are fixed by the context in which the CS value occurs. CS is used for coded attributes that have a single HL7-defined value set. |
| CV | Coded Value - Coded data, specifying only a code, code system, and optionally display name and original text. Used only as the data type for other data types' properties. |
| CE | Coded with Equivalents - Coded data that consists of a coded value (CV) and, optionally, coded value(s) from other coding systems that identify the same concept. Used when alternative codes may exist. |

The semantics represented by domain-specific terms within at least one terminology may form a terminology model, which is separate from but related to the semantics represented by the common information model (RIM). HL7 v3 provides a methodology for binding the terminology and information models by binding RIM structures and domain-specific terms. For example, attributes associated with RIM Acts may be bound to coded data types with values represented by healthcare industry-standard code systems such as SNOMED-CT.

Since the HL7 v3 standard is well known in the art, discussion of further details of the HL7 v3 standard is omitted here.

2. Healthcare Transaction Framework

Figure 3:
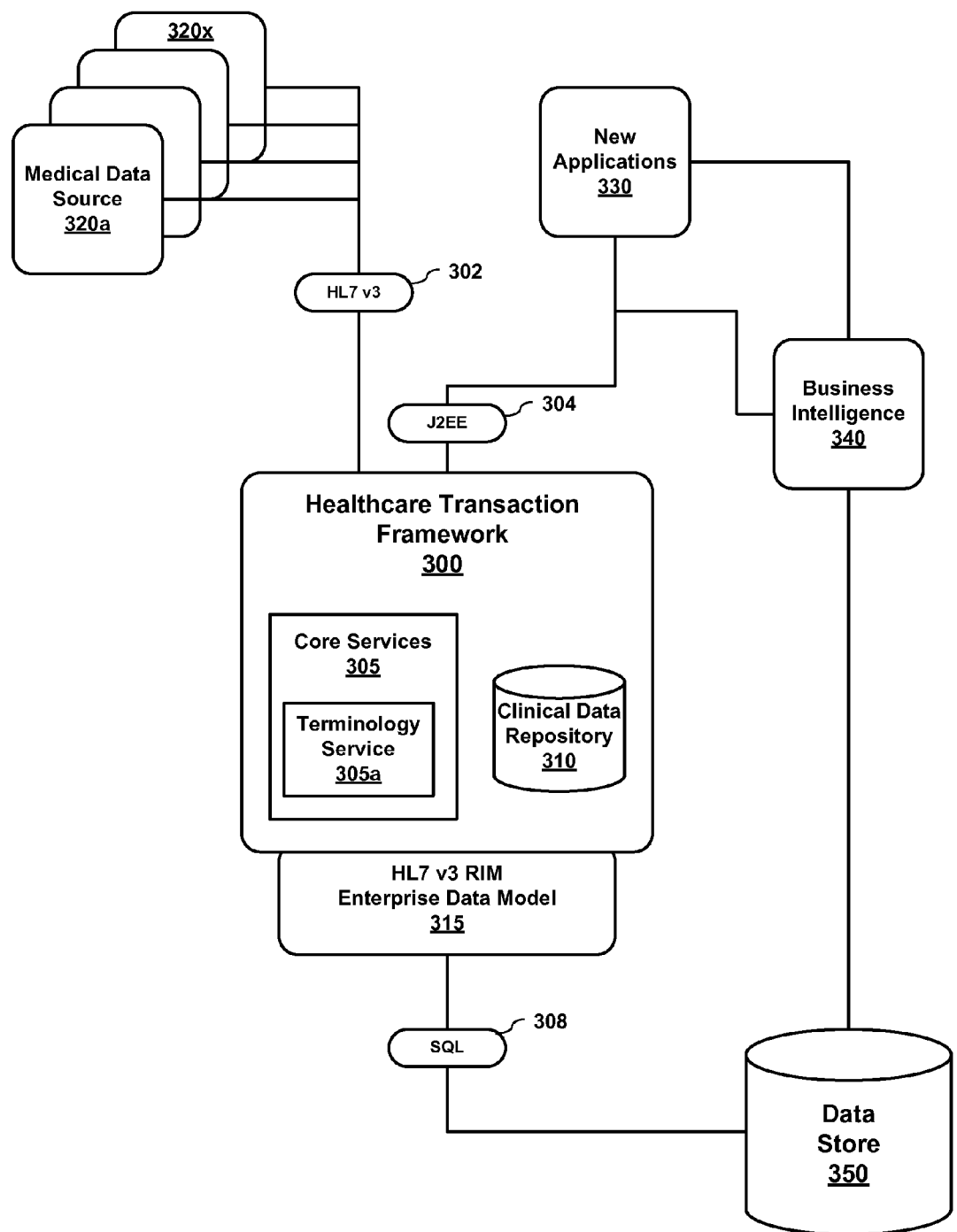
FIG. 3 depicts an exemplary healthcare transaction framework according to various embodiments of the invention.

FIG. 3 depicts an exemplary healthcare transaction 300 according to various embodiments of the invention. Implemented within a healthcare institution's IT infrastructure, a healthcare transaction framework 300 may provide the foundation for information sharing between healthcare providers, insurers, pharmaceutical companies, and clinical research institutions.

In various embodiments, a healthcare transaction framework 300 supports an HL7 v3 RIM enterprise data model 315. Medical information is represented as RIM data structures, and is stored persistently as structured records in a data repository 350, such as a data warehouse. In embodiments, the data repository 350 comprises one or more relational databases and the stored structured records may be accessed via a SQL 308 query.

In embodiments, a healthcare transaction framework 300 deployed at a healthcare institution may enable HL7 v3-compliant 302 aggregation of information in the data repository 350. This information may be derived from a set of disparate medical data sources comprising a set of internal data sources, such as a clinical data repository 310 within the healthcare institution's IT infrastructure, and a set of external data sources (320a through 320x) such as hospitals, primary care providers, social services agencies, insurance providers, pharmacies, and independent consultants. In embodiments, a healthcare transaction framework 300 may provide programmatic and/or web-based access to the data repository 350 via enterprise Java (J2EE) 304 application programming interfaces (APIs). These APIs enable the integration of healthcare applications 330 (e.g., display of an integrated view of patient clinical results, computerized physician order entry, and creating, viewing, tracking, and processing simple or complex clinical documents) and business intelligence services 340 (e.g., analysis and reporting of clinical and administrative measures and analysis and reporting of key claims-based financial measures) via IT applications such as a portal.

In embodiments, a healthcare transaction framework 300 comprises a set of core services 305 that may comprise message management, security and auditing, person services, configuration, workflow integration, and a terminology service 305a. In embodiments, a terminology service 305a manages the set of terminologies supported by an implementation of the healthcare transaction framework 300. As previously described, terminologies are concept-based, and the set of supported terminologies may include HL7 terminologies, industry standard terminologies (such as SNOMED-CT and ICD-9), and custom terminologies defined within the healthcare transaction framework 300 implementation. As previously described, each terminology is associated with a code system and, in embodiments, each code may be assigned a unique identifier. In embodiments, a terminology service 305a may maintain a code repository of all of the managed codes. There may be overlaps among the vocabulary domains represented by the managed codes, and, in embodiments, a terminology service 305a code repository may include mapping definitions that represent inter-terminology and intra-terminology semantic relationships. In embodiments, a terminology service may include an intra-terminology version management system. In embodiments, the terminology service 305a maintains semantic mapping and version control definitions of the codes in the code repository.

B. A Concept-Based RIM Query Service

In embodiments, a healthcare transaction framework 300 may provide a RIM query service API to enable applications 330 and/or business intelligence services 340 or both to have programmatic access and/or web-based access to structured records in the data repository 350. In embodiments, the RIM query service API may be a set of Java interfaces 304.

Figure 4:
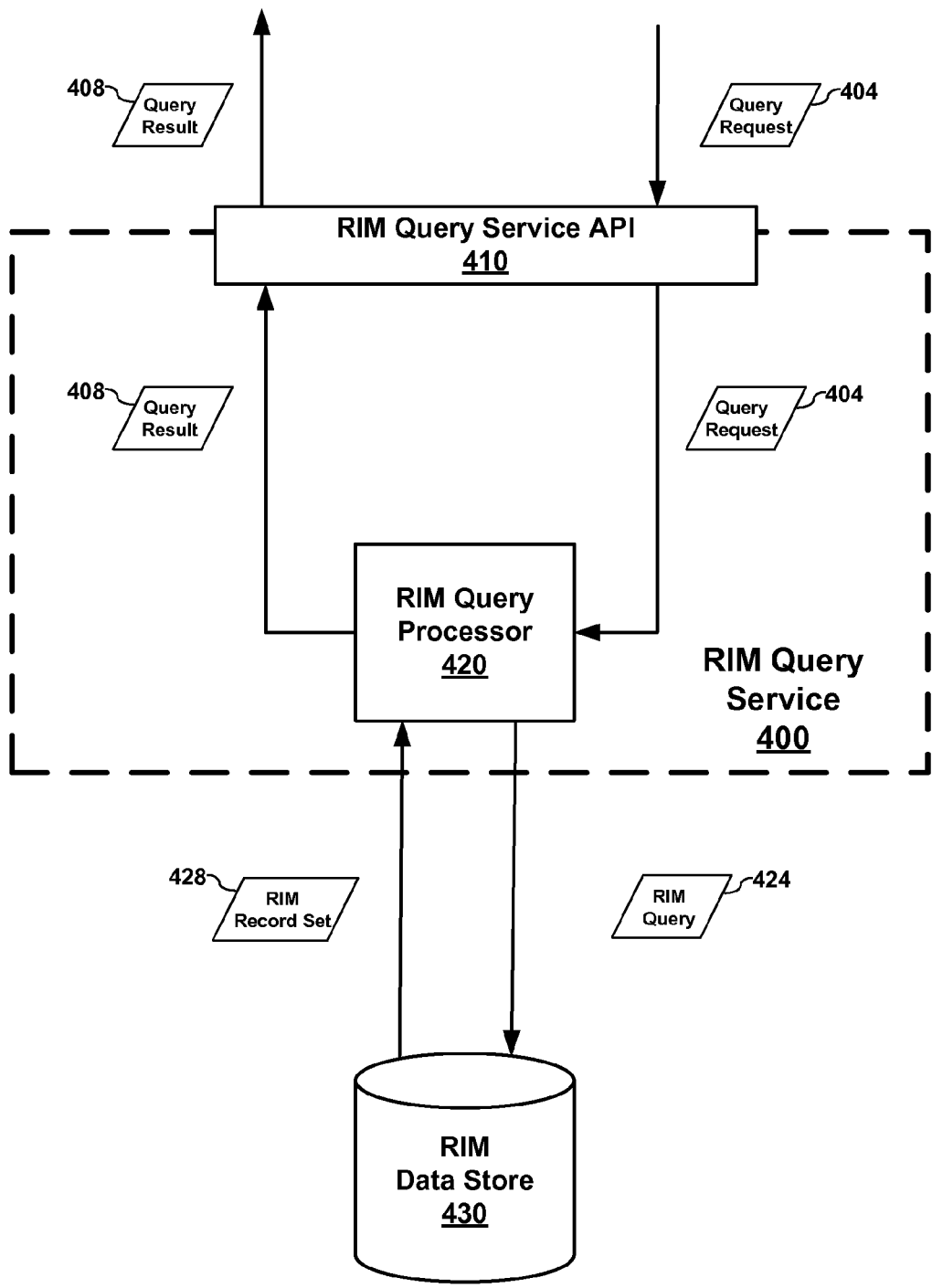
FIG. 4 depicts an exemplary RIM query service according to various embodiments of the invention.

FIG. 4 depicts an exemplary RIM query service 400 according to various embodiments of the invention. A query request 404 received at a RIM query service API 410 may comprise a set of search criteria (e.g., a set of attributes). In embodiments, a RIM query processor 420 uses the set of search criteria to generate a SQL RIM query 424 having at least some of the search criteria as parameters in the query predicates. The SQL RIM query 424 is submitted to a RIM data store 430 which, in embodiments, may contain aggregated healthcare information stored as structured records 350. In embodiments, the RIM query 424 may be used to extract a RIM structured record set 428 specified by the set of search criteria. In embodiments, a query result 408 comprising the RIM record set 428 may be returned to a requester via the RIM query service API 410.

In embodiments, a query request 404 typically may result in a generated SQL RIM query 424 with a direct equality predicate that compares a search criterion attribute value to a value within a structured record to determine if they are equal. In embodiments, the set of search criteria attributes supplied in the query request 404 may comprise coded attributes (e.g., HL7 v3 attributes with CD, CE, CS, and CV data types as listed in Table 1). The processing of a SQL RIM query 424 having a direct equality predicate containing a coded attribute value may not return the expected query result. Due to overlaps among the vocabulary domains represented by the set of codes within a code repository, determination of the value of a coded data type may depend on mapping definitions managed by the terminology service 305a. For instance, various stored values of a coded attribute may have been encoded using broader codes or narrower codes than the code of the search criterion value, or may have been encoded using equivalent codes from the same or different code systems as the code of the search criterion value.

In embodiments, a RIM query service 400 may leverage the terminology service 305a in order to handle an input query request 404 that specifies concept-based semantics and comprises coded search criteria (a "concept query request"). Examples of concept-based semantics that may be specified in a concept query request include the retrieval of all concepts that are equivalent to a given concept, and the retrieval of all concepts that comprise a classification.

Figure 5:
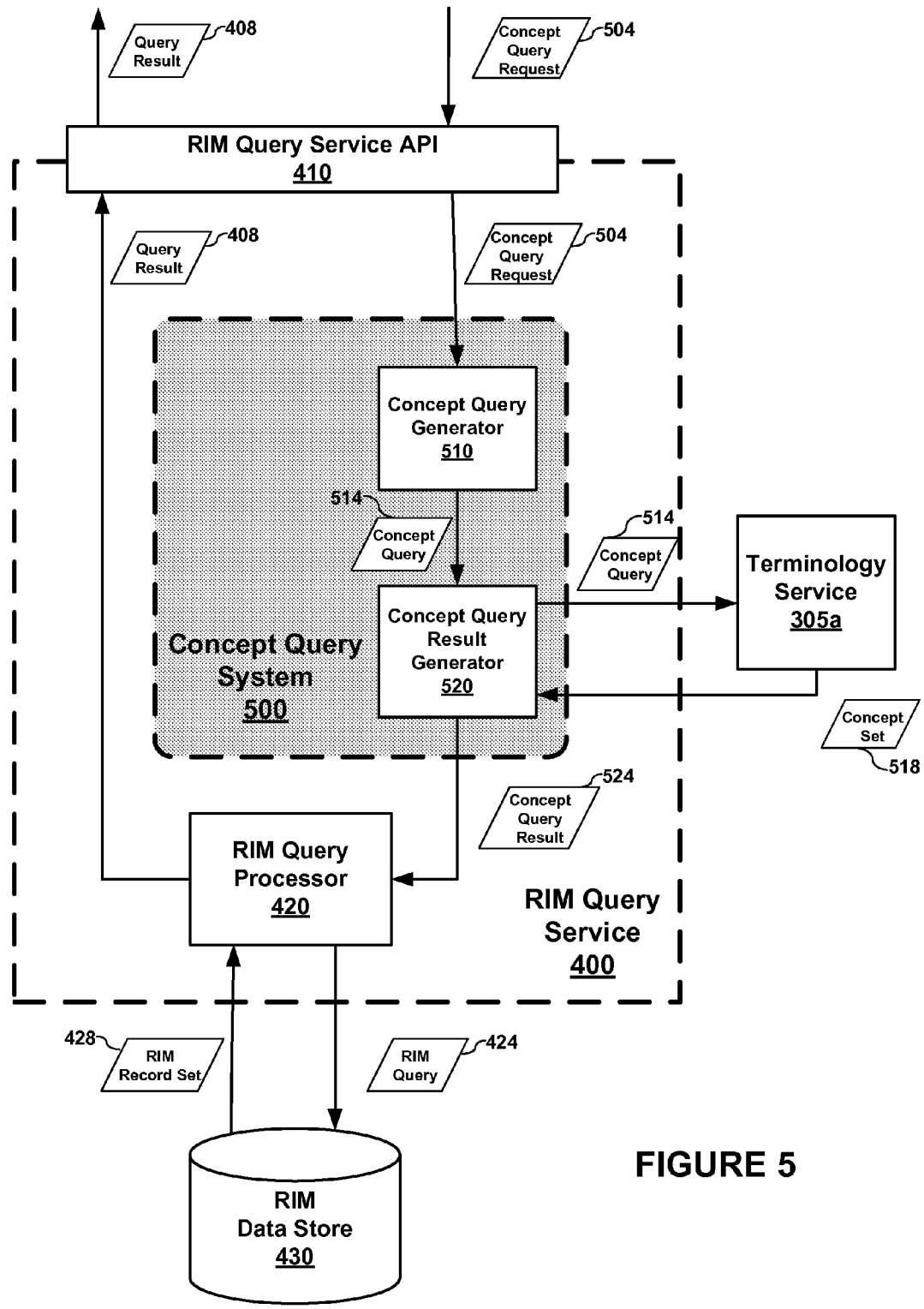
FIG. 5 depicts a RIM query service comprising a concept query system according to various embodiments of the invention.

FIG. 5 depicts a RIM query service 400 comprising a concept query system 500 to provide support for handling RIM concept query requests according to various embodiments of the invention. A concept query request 504 may specify concept-based semantics, and may comprise a set of coded search criteria. In embodiments, the specified concept-based semantics and set of coded search criteria may be received by a concept query generator 510 and used to configure a concept query 514. In embodiments, a concept query result generator 520 submits the concept query 514 to a terminology service 305a in order to extract a set of concepts 518 that are associated with the set of coded search criteria. The set of concepts 518 is constructed dynamically by the terminology service 305a based on its current terminology model definitions. In embodiments, concept query result generator 520 constructs a concept query result 524 based on the retrieved set of concepts 518.

In embodiments, a RIM query processor 420 constructs a RIM query definition comprising predicates based on the set of concepts 518 comprising the concept query result 524. In embodiments, the RIM query processor 420 may use the RIM query definition to generate a RIM SQL query 424 to retrieve a structured RIM record set 428 stored within a RIM data store 430. In embodiments, a query result 408 comprising the RIM record set 428 may be returned via the RIM query service API 410.

1. Concept-Based Query Using Equivalence

Concept equivalence is the unification of semantically redundant content in a terminology repository. In embodiments, two concepts belonging to the same coding scheme have semantic equivalence if they have identical meanings. In embodiments, concepts from different coding schemes, or concepts from different versions of the same coding scheme, are semantically equivalent if they are determined to have mapping equivalence (i.e., they are determined to have explicit cross map equivalences based upon map sets defined within the terminology repository).

In an exemplary scenario, a direct equality RIM query 424 to retrieve from the RIM data store 430 the data records representing all encounters where the admitting diagnosis is "hypertension" may evaluate the value coded attribute for a RIM Observation (OBS) 140 representing an admission diagnosis in order to select the instances where the value coded attribute was equal to "hypertension." Over time, instances of RIM OBS in the RIM data store 430 representing the diagnosis of "hypertension" may have come to have the value coded attribute bound to concepts from different versions of a coding scheme, or bound to concepts from different coding schemes (e.g., "high blood pressure," "blood pressure with systolic value greater than X"). In this case, a RIM query 424 to extract diagnoses with the value coded attribute directly equal to "hypertension" may not result in the extraction of all of the relevant admission diagnoses. In order to find all equivalent instances of "hypertension" diagnoses, an application programmer or end user would need to look up and identify the terminology concept equivalences to "hypertension" that have been defined within the system, and then explicitly structure a query request 404 to generate a RIM query 424 that contains a simple equality predicate for each of the identified concepts. Building a RIM query from explicitly identified concepts in this way is time consuming and is likely to produce invalid or incomplete results due to concept identification errors. In addition, each generated RIM query 424 represents concepts that are identified based on a snapshot of the current set of equivalence definitions, and those definitions may change over time. To insure that a generated RIM query 424 reflects the current equivalence definitions, a new query request 404 specifying a current set of identified concepts would have to be constructed for each access of the RIM data store 430.

FIG. 5 depicts a RIM query service 400 comprising a concept query system 500 to provide support for code equivalences in RIM concept query requests according to various embodiments of the invention. In embodiments, an equivalence concept query request 504 specifies equivalence semantics and comprises a set of equivalence criteria which includes at least one concept (a seed concept). The set of equivalence criteria need only identify any single seed concept within a set of equivalent concepts in order to retrieve the full set of equivalent concepts 518. In the previously described scenario, "hypertension" would be the seed concept supplied in the concept query request 504. In embodiments, the concept query system 500 leverages the terminology service 305a to retrieve the set of concepts 518 that are equivalent to the seed concept based on the current terminology contents equivalence definition.

In embodiments, the set of equivalence criteria supplied in the concept query request 504 may further comprise an "equivalence type" that is used to specify the kind of equivalence definition to be applied by the terminology service 305a in retrieving the set of equivalent concepts. For example, in embodiments, equivalence type may specify equivalence definitions such as the application of semantic equivalence between concepts in the same coding scheme, or the application of a mapping equivalence (cross map) between concepts in different coding schemes.

In embodiments, the set of equivalence criteria may further comprise a specification of the bounds of the equivalence definition domain to be applied in retrieving the set of equivalent concepts 518. For example, an equivalence definition domain boundary may be defined to be within a single code system, or it may be defined to span across multiple code systems. Additionally, in embodiments, an equivalence definition boundary may place a limit on the number of equivalence mappings that can be traversed to find equivalent concepts.

In embodiments, specification of an equivalence definition domain boundary may further comprise specifying an equivalence context (usage context) that restricts equivalences to those that are interesting or appropriate in the context of one process but not in other processes. For example, a billing department may simplify their processing by identifying many variants of a disease as "equivalent," while clinical researchers may be interested in the fine clinical details of cases which would not be discriminated in a query using the billing department's context. In embodiments, each group would be able to specify an equivalence context that represents its equivalence mapping requirements. In another example, to generate a report showing the high level breakdown of causes of death, a new equivalence context MORBIDITY may be created, resulting in a set of equivalence maps that would allow many diseases that are not normally equivalent to be made equivalent in the context of morbidity.

Figure 7:
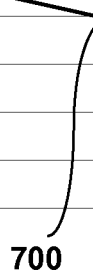
FIG. 7 illustrates an exemplary inter-version equivalence definition according to various embodiments of the invention.
Figure 8:
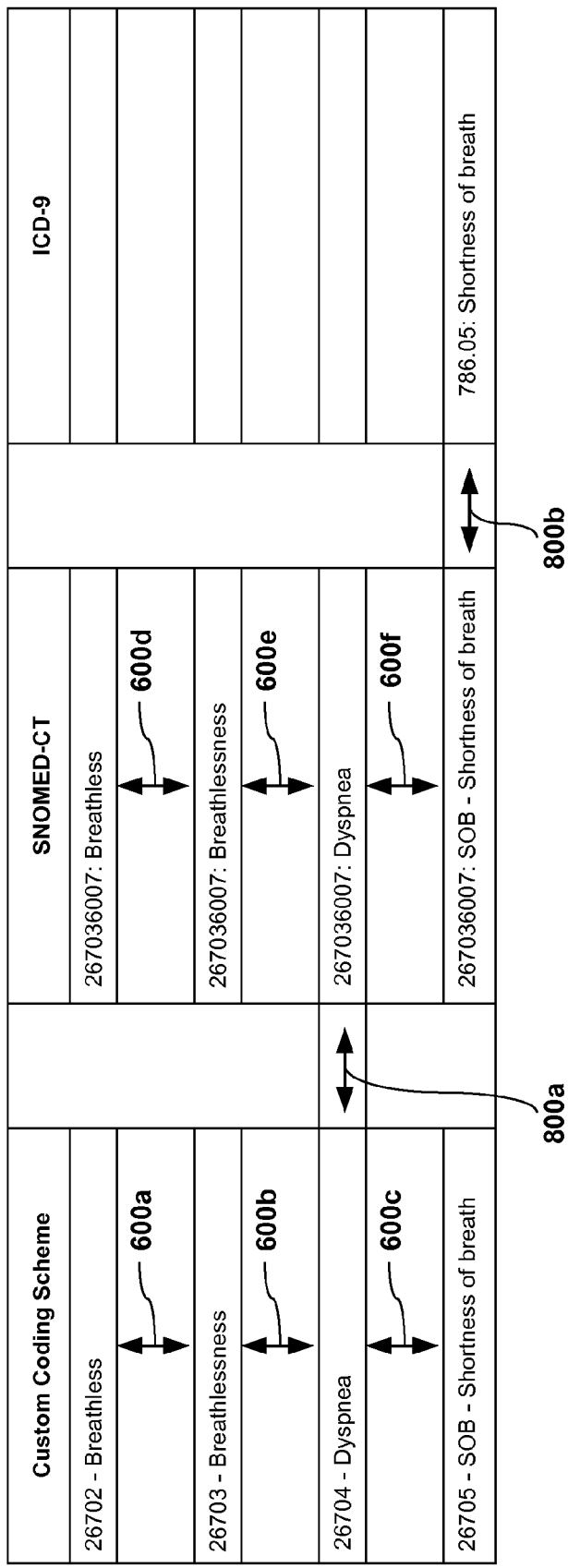
FIG. 8 illustrates an exemplary inter-terminology equivalence definition according to various embodiments of the invention.

FIGS. 6, 7, and 8 depict exemplary scenarios (for illustration and not limitation) of three types of equivalence mapping that may be defined within a code repository maintained by a terminology service 305*a* according to various embodiments of the invention.

FIG. 6 illustrates an example of intra-version equivalence 600*a-c* for codes representing the same concept within the same terminology (code system), which is a custom coding scheme in this example, according to various embodiments of the invention. In embodiments, a concept query request 504 specifying semantic equivalence and the seed code "26704—Dyspnea" results in a concept query result 524 containing the equivalent codes Breathless, SOB, Dyspnea, and Breathlessness. A RIM query 424 generated from that concept query result 524 can be used to extract records 428 from the RIM data store 430 of all of the patients reporting with Breathless, SOB, Dyspnea, and Breathlessness.

FIG. 7 illustrates an example of inter-version equivalence within the same terminology (code system), a custom coding scheme in this example, according to various embodiments of the invention. In this example, a hospital uses a custom coding scheme to capture the symptoms provided by the patients relating to the respiratory system. In version 2.0 of the custom coding scheme, it was decided that "26702—Breathless" would be retired and that an inter-version equivalence 700 would be created between version 1.0 "26702—Breathless" and version 2.0 "26703—Breathlessness." In this example, the inter-version equivalence 700 is a mapping equivalence (cross map) within the same coding scheme. In embodiments, a concept query request 504 specifying mapping equivalence, an equivalence definition domain boundary that is limited to a single code system, and the seed code "26704—Dyspnea" should result in a concept query result 524 containing the equivalent version 2.0 codes SOB, Dyspnea, and Breathlessness and the version 1.0 code Breathless. The RIM query 424 generated from that concept query result 524 should be used to extract records 428 from the RIM data store 430 of all of the patients reporting with SOB, Dyspnea, and Breathlessness, and also pick up old records of patients reporting with Breathless.

FIG. 8 illustrates an example of inter-terminology equivalence according to various embodiments of the invention. A hospital loads three terminologies (ICD-9, SNOMED-CT, and a custom coding scheme) into its terminology service 305*a* code repository, and has persistent RIM data records 430 that have been acquired from multiple medical sources (320*a-x*) and represented in all of these terminologies. There is both intra-terminology (direct) equivalence (600*a-c* and 600*d-f*) and inter-terminology (mapping) equivalence (800*a* and 800*b*) defined. In embodiments, a concept query request 504 specifying mapping equivalence, an equivalence domain boundary that spans across multiple code systems, and the seed code "26704—Dyspnea" should result in a concept query result 524 containing all of the equivalent codes for Breathless, SOB, Dyspnea, and Breathlessness that have been defined in the custom coding scheme and SNOMED-CT, as well as the Shortness of Breath code defined in ICD-9. The RIM query 424 generated from that concept query result 524 should be used to extract records 428 from the RIM data store 430 of all of the patients reporting with Breathless, SOB, Shortness of Breath, Dyspnea, and Breathlessness as represented in all 3 codes.

2. Concept-Based Query Using Classification

In embodiments, the RIM records stored in a data store 350 may be further organized using higher-order classification concepts (i.e., concepts not stored in the records themselves) that may be based on a variety of industry-standard and proprietary classification systems. These higher-order classifications may be derived from systematic terminologies (defined by an organized body, such as SNOMED-CT), or they may be user-defined (e.g., designed to achieve a particular goal within the context of the user's system). In embodiments, providers and other users of healthcare systems may classify terminology content to enable ease of viewing, to facilitate selection of concepts, and to support class-based querying of information.

In embodiments, higher-order classifications may be constructed based on the terminology contents (i.e., concepts described by a set of code systems) managed by a terminology service 305*a*. A classification may be a concept container that is associated with a unique identifier and stored within the terminology contents. All concepts associated with the concept container have an IS-A association with the container (i.e., each of the concepts is a specialization of the container). For example, in embodiments, an "antibiotics" classification is a bin of concepts, each of which is classified as an antibiotic. In embodiments, a classification container itself may have concept characteristics, such as having multiple equivalent descriptions. In embodiments, the contents of a classification may be defined declaratively via a concept query. For example, a query "Add concept X and all its descendents to classification Y" adds to classification Y the concept X and all concepts that have an IS-A relationship to concept X in its native terminology.

In various embodiments, higher-order classifications may be hierarchical (i.e. contain sub-classifications). For example, the "antibiotics" classification may be nested under the "critical drug" classification, with the result that any "antibiotic" also may be considered to be a "critical drug." In embodiments, containment of a concept at any level of a constructed hierarchy may be tested via a single concept query. For example, the query predicate "classification Y contains (X)" tests whether X is contained in classification Y or in any classification below classification Y at any level of a constructed hierarchy of classifications.

In an exemplary scenario, a RIM query request 404 to retrieve all medication administration events where the ENTITY.CODE is equal to "penicillin" may be submitted. As there are a variety of different products that contain penicillin, a RIM query 424 generated from the query request 404 that has a direct equality predicate specifying "penicillin" may not result in the retrieval of records from the RIM data store 430 that are associated with all of the relevant products. However, a concept query request specifying "the class of products containing penicillin" would insure that all of the relevant records are retrieved. In another example, patients receiving oral anticoagulants such as Warfarin must be regularly monitored to avoid bleeding problems. In a system that manages patient medications, an assigned person must be either presented with, or be able to, formulate a list of patients that are being administered this class of anticoagulants so that the appropriate lab orders and notifications can be created. A concept query request specifying "the class of anticoagulants containing Warfarin" may retrieve all of the relevant medications that lie within this class of anticoagulants.

Typically, accessing all of the RIM concepts within a higher-order classification via a query would require an application programmer or end user to first identify the concepts that belong to the classification (i.e., explicitly identify all concepts that have an IS-A association with the classification), and then either input a set of separate direct equality query requests 404, each specifying a single identified concept as a search criterion, or input a single direct equality query request 404 that specifies all of the identified concepts as a set of search criteria. Identifying concepts that belong to a classification may be time-consuming and could lead to invalid query results if identification errors are made. Additionally, since high order terminology concept definitions of equivalence and classification may change over time, a classification concept query request 404 would need to be re-generated each time to insure that the concepts were identified based on current terminology definitions. If a classification query request 404 contains coded attributes (e.g., HL7 v3 attributes with CD, CE, CS, and CV data types as listed in Table 1), the attribute values might require checking of their membership in some larger category of codes defined within a higher-order classification scheme within the terminology contents, so a resulting RIM query 424 using only the input coded attribute values may not retrieve all of the relevant RIM records associated with the classification.

FIG. 5 depicts a RIM query service 400 comprising a concept query system 500 to provide support for class-based RIM query requests according to various embodiments of the invention. In embodiments, a user may query for a set of concepts contained within a higher-order classification by submitting a classification concept query request 504 that comprises an identifier corresponding to the higher-order classification container. In embodiments, the concept query system 500 leverages the terminology mappings to identify classification-based relationships within the terminology contents managed by a terminology service 305a. In embodiments, a set of concepts 518 associated with the classification identifier supplied in a concept query request 504 is retrieved.

Turning to the example of intra-version equivalence depicted in FIG. 6, adding any one of the concepts to a "Respiratory System Complaints" classification container would result in each of the concepts being associated (i.e. assigned an IS-A relationship) with the classification container because of the equivalence relationship of the concepts. In embodiments, a classification concept query request 504 comprising the classification identifier "Respiratory System Complaints" should result in a concept query result 524 containing the codes Breathless, SOB, Dyspnea, and Breathlessness. The RIM query 424 generated from that concept query result 524 should be used to extract records 428 from the RIM data store 430 of all of the patients reporting with Breathless, SOB, Dyspnea, and Breathlessness.

C. System Implementations

Figure 9:
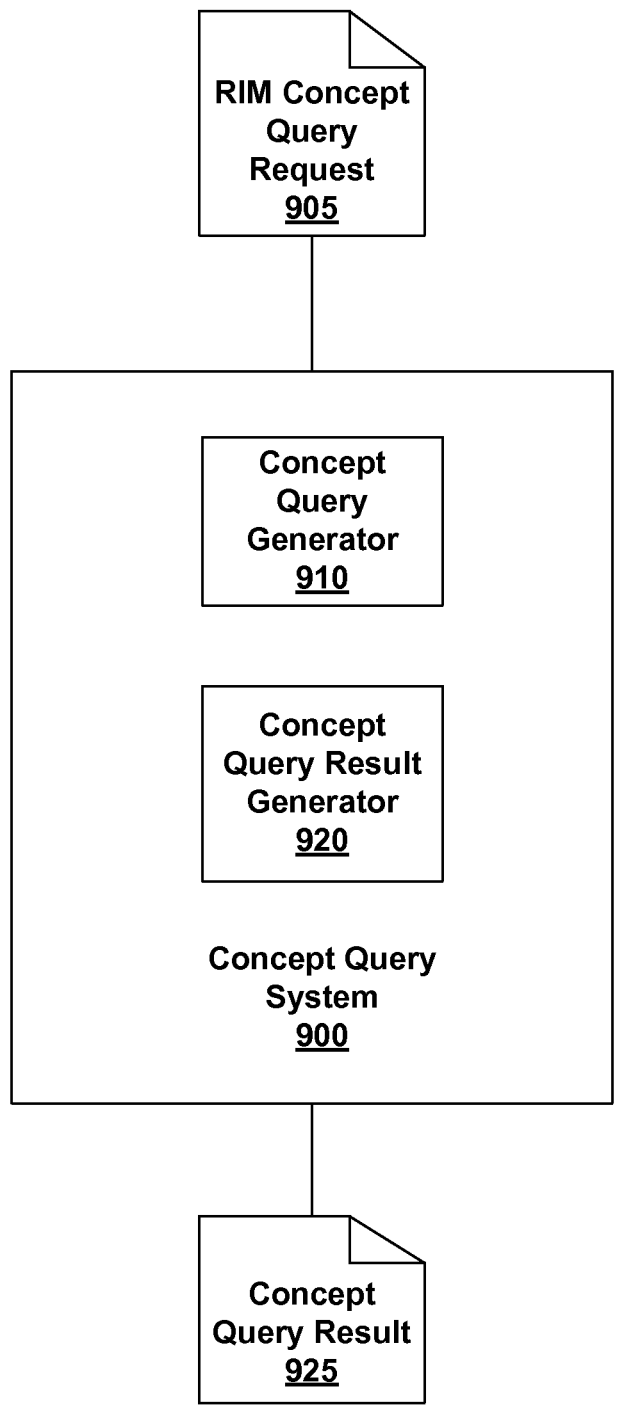
FIG. 9 depicts a block diagram of a concept query system according to various embodiments of the invention.

FIG. 9 depicts an embodiment of concept query system 900 for generating a concept query result 925 based on a set of criteria from a received RIM concept query request 905 according to various embodiments of the invention. In embodiments, the set of criteria may comprise coded attributes. In embodiments, concept query system 900 comprises a concept query generator 910 and a concept query result generator 920. Various embodiments of a RIM query service 400 may comprise an embodiment of concept query system 900 for handling a RIM concept query request 504 as illustrated in FIG. 5.

In embodiments, concept query generator 910 receives a RIM concept query request 905 comprising specified concept semantics and a set of search criteria (i.e., a set of attributes). In embodiments, the input set of search criteria supplied in the concept query request 905 comprises coded attributes (e.g., HL7 v3 attributes with CD, CE, CS, and CV data types as listed in Table 1). As previously described, an HL7 v3 attribute binding to a data type defines a semantic relationship, and the domain of the code affects the meaning of the record. The RIM backbone classes each have a set of attributes that take values having certain data types, and the meaning of a value is determined by the name of the attribute with which it is associated In embodiments, a terminology service 305a comprising a core service within a healthcare transaction framework 300 may maintain a repository of the managed codes (vocabulary domains) within the framework. There may be overlaps among the vocabulary domains, and, in embodiments, the terminology service 305a code repository may include defined mappings between codes that represent inter-code and intra-code semantic relationships, such as the exemplary relationships depicted in FIGS. 6, 7, and 8.

In embodiments, an equivalence concept query request 905 may include a set of search criteria comprising a seed concept, an equivalence type, and equivalence depth. This set of search criteria is received by a concept query generator 910. In embodiments, the concept query generator 910 may use the set of search criteria to configure an equivalence concept query 514 comprising the seed concept.

In embodiments, a classification concept query request 905 may comprise a class identifier associated with a higher-order classification container defined within the terminology content managed by the terminology service 305a. In embodiments, the concept query system 500 leverages defined terminology concept mappings to identify class-based relationships within the terminology content. In embodiments, the concept query generator 910 may configure a classification concept query 514 comprising the received class identifier.

In embodiments, concept query result generator 920 receives a concept query 514 and submits the concept query 514 to a terminology service 305a in order to extract a set of concepts 518 from terminology content managed by the terminology service 305a. In embodiments, the set of concepts 518 extracted in response to a submitted equivalence concept query 518 are a set of equivalent concepts 518 comprising the seed concept. The set of equivalent concepts 518 is constructed dynamically by the terminology service 305a based on its current equivalence definitions. In embodiments, the set of concepts 518 extracted in response to a submitted classification concept query 518 are concepts associated with a higher-order classification container having the specified class identifier. The set of associated concepts 518 is constructed dynamically by the terminology service 305a based on the current classification-based relationship mappings within its managed terminology content.

In embodiments, a concept query result generator 920 constructs a concept query result 925 based on the retrieved set of associated concepts 518. In embodiments, a SQL RIM query 424 comprising predicates based on the concept query result 925 may be generated by a RIM query processor 420.

D. Method Implementations

The following sections describe embodiments of methods for receiving a concept query request and generating a structured database query in response according to various embodiments of the invention. The method embodiments may be implemented in embodiments of concept query system 900.

1. Method for Handling an Equivalence Concept Query Request

Figure 10:
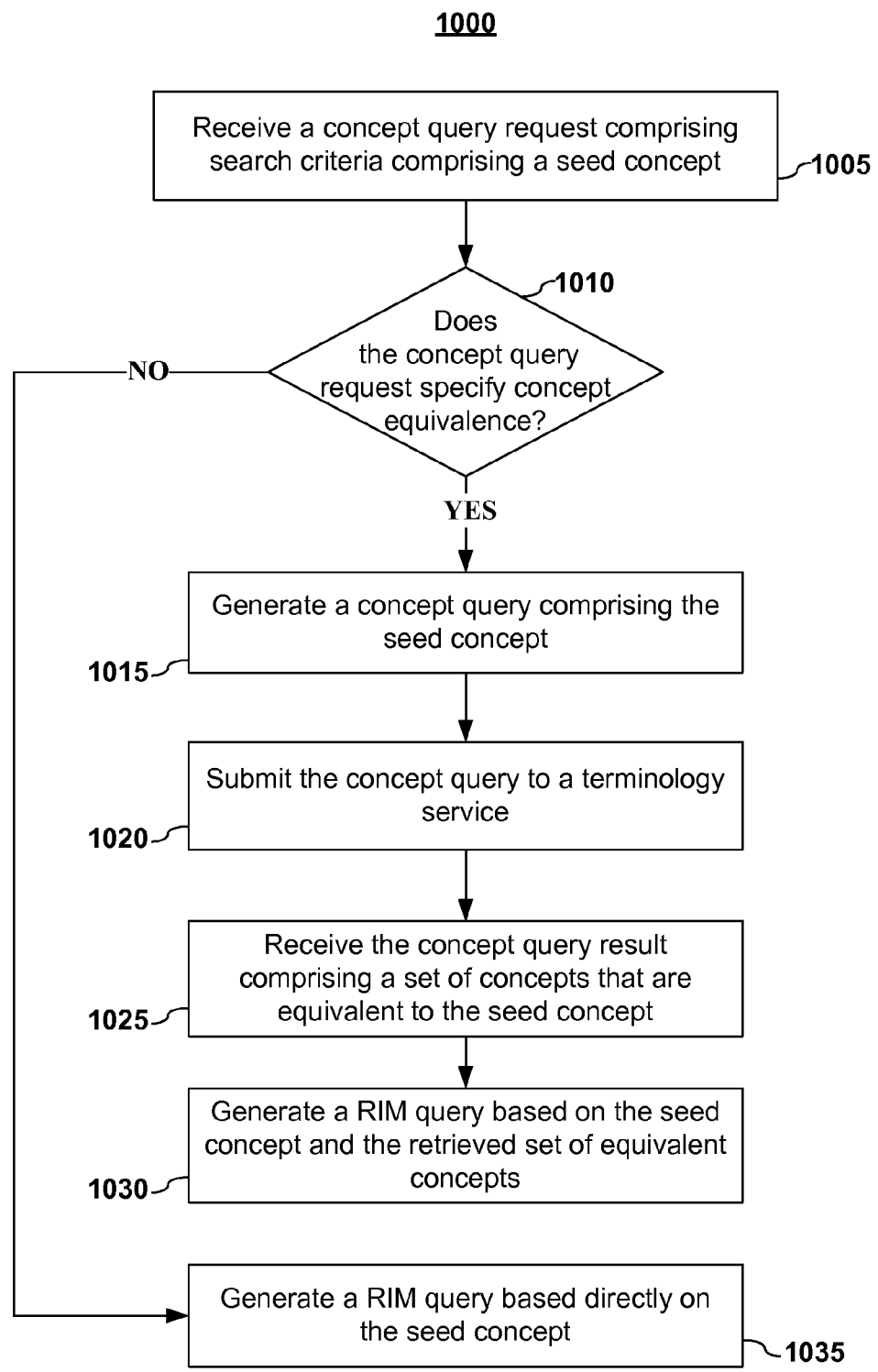
FIG. 10 depicts a method for handling an equivalence concept query request according to various embodiments of the invention.

FIG. 10 depicts a method 1000 for handling an equivalence concept query request according to various embodiments of the invention. Method 1000 may be implemented in embodiments of concept query system 900.

As previously described, an equivalence concept query request 504 comprises a set of search criteria that are submitted to a terminology service 305a in order to extract a set of concepts 518 that are equivalent to a seed concept. In embodiments, the set of search criteria comprises coded attributes (e.g., HL7 v3 attributes with CD, CE, CS, and CV data types as listed in Table 1). In embodiments, the terminology mappings in the terminology content managed by the terminology service 305a are leveraged in order to determine an equivalence definition that is used for retrieving the set of equivalent concepts 518 from the terminology content.

In embodiments, the set of search criteria supplied in a received 1005 equivalence concept query request 504 comprises a seed concept and may further comprise a specification of the bounds of the equivalence definition domain to be applied in retrieving the set of equivalent concepts 518. An equivalence definition domain boundary may be defined to be within a single code system, or it may be defined to span across multiple code systems. For example, in embodiments, the equivalence definition domain boundary may be specified by an "equivalence depth" boolean flag. If the flag value is true, all concepts are considered that are either directly equivalent to the seed concept (explicitly asserted to be equivalent through a cross map or a change file associated with version control) or transitively equivalent to the seed concept (inferred to be equivalent by transitively chaining direct equivalence assertions). If the flag value is false, only concepts that are directly equivalent to the seed concept are considered (i.e., do not use transitive chaining).

In embodiments, specification of an equivalence definition domain boundary may further comprise defining an equivalence context (usage context) that restricts equivalences that are interesting or appropriate in the context of one process but not in other processes. For example, in embodiments, a default usage context may be SYSTEM (i.e., use all mappings defined within a code repository), and the default value may be overridden by the specification of a defined usage context.

In embodiments, the set of equivalence criteria may further comprise an "equivalence type" that is used to specify the kind of equivalence definition to be applied. In embodiments, equivalence type may be represented as an enumerated constant (enum) having values such as (for illustration and not limitation) EQUIVALENCE_TYPE_SEMANTIC (apply semantic equivalence between concepts in the same coding scheme); and EQUIVALENCE_TYPE_MAPPING (apply a mapping (cross map) between concepts in different coding schemes as well as semantic equivalence between concepts in the same coding scheme).

In embodiments, if a received concept query request 1005 specifies concept equivalence 1010 and comprises a seed concept, then an equivalence concept query 514 comprising the seed concept is generated 1015 and submitted 1020 to a terminology service 305a.

In embodiments, a query result comprising a set of equivalent concepts 518 comprising the seed concept is received 1025 from the terminology service 305a. Turning to the exemplary intra-terminology equivalence (600a-c) definition illustrated in FIG. 6, a concept query 514 specifying semantic equivalence and the seed code "26704—Dyspnea" should return a set of directly equivalent concepts 518 containing the codes for Breathless, SOB, Dyspnea, and Breathlessness. Turning to the exemplary FIG. 8 equivalence definition exhibiting intra-terminology equivalence (600a-c and 600d-f) and inter-terminology equivalence (800a and 800b), a concept query 514 specifying mapping equivalence, an equivalence domain boundary indicating both direct and transitive semantic equivalence, and the seed code "26704—Dyspnea" should return a concept query result 524 containing all of the illustrated symptom codes. In the example, "Shortness of breath" in ICD-9 is directly equivalent to "SOB—Shortness of breath" in SNOMED-CT via cross map 800b, and it is transitively equivalent to "Breathless" SNOMED-CT.

In embodiments, a structured database query (e.g., a SQL RIM query 424) that comprises predicates associated with the retrieved set of equivalent concepts 518 may be generated 1030. In various embodiments, a concept query result 524 generated from the retrieved set of equivalent concepts 518 is provided to a structured database query processor 420 within a query service 400. In embodiments, the structured database query processor 420 may use the concept query result 524 to generate a structured database query 424 in order to extract a data record set 428 from a data repository 430.

In embodiments, if the received concept query request does not denote the application of semantic equivalence concept mapping 1010, then no equivalence concept query 514 is generated. For example, in embodiments, no application of semantic equivalence concept mapping may be denoted in a concept query by its associated search criteria comprising an equivalence type enum having a value of EQUIVALENCE_TYPE_EXACT_CONCEPT. In this case, no concept-based semantic processing is applied to the seed concept, and the generated 1035 structured database query 424 may comprise a direct equality predicate applied to the seed concept.

2. Method for Handling a Classification Concept Query Request

Figure 11:
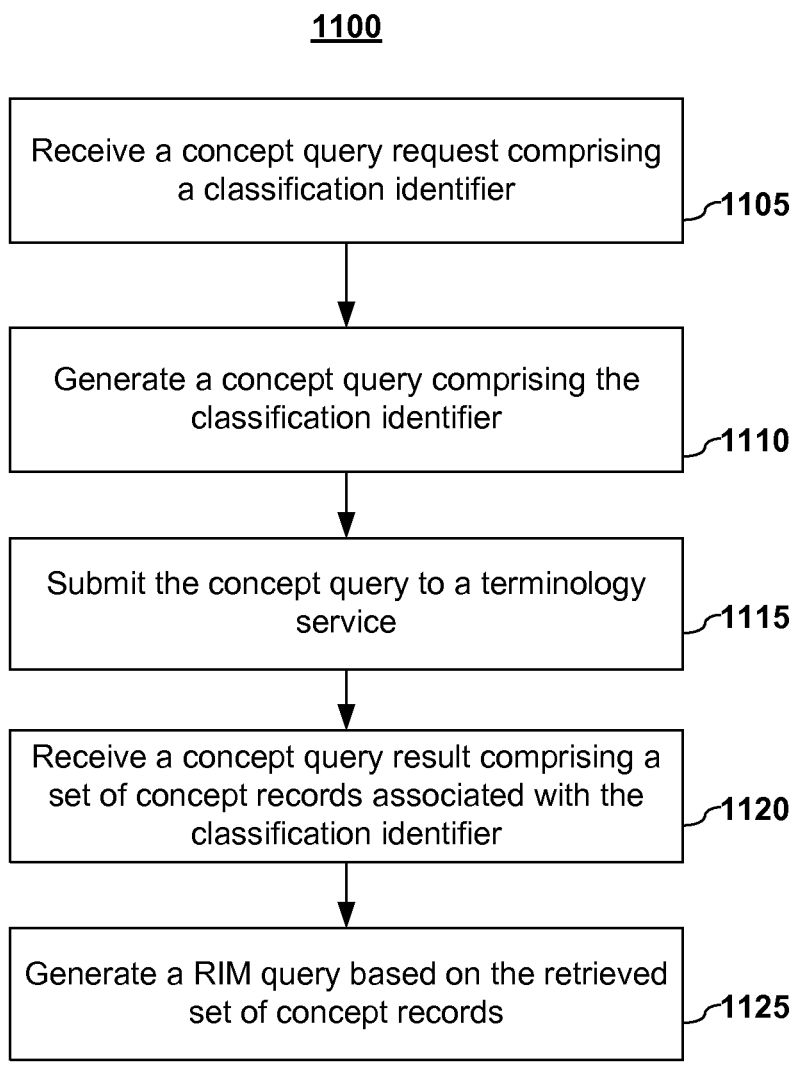
FIG. 11 depicts a method for handling a classification concept query request according to various embodiments of the invention.

FIG. 11 depicts a method 1100 for handling a classification concept query request according to various embodiments of the invention. Method 1100 may be implemented in embodiments of concept query system 900.

In embodiments, if a received concept query request 1105 specifies a set of concepts contained within a higher-order classification, then a classification concept query 514 comprising an identifier corresponding to a higher-order classification container is generated 1110 and submitted 1115 to a terminology service 305a. In embodiments, the classification identifier and/or the set of associated concepts may be represented by coded attributes (e.g., HL7 v3 attributes with CD, CE, CS, and CV data types as listed in Table 1). In embodiments, the terminology service 305a leverages terminology mappings to identify classification-based relationships within the terminology content.

In embodiments, a query result comprising a set of associated concepts 518 having an IS-A relationship to the higher-order classification is received 1120 from the terminology service 305a. As previously described, higher-order classifications may be hierarchical, and containment of a concept at any level of a constructed hierarchy may be tested via a single concept query.

Turning to the example of intra-version equivalence depicted in FIG. 6, each of the entries additionally may have been defined to have an IS-A relationship to a "Respiratory System Complaints" classification container. In embodiments, a classification concept query request 514 comprising the classification identifier "Respiratory System Complaints" would return a concept set 518 containing the codes for Breathless, SOB, Dyspnea, and Breathlessness.

In embodiments, a structured database query (e.g., a SQL RIM query 424) that comprises predicates associated with a concept set 518 may be generated 1125. In various embodiments, a concept query result 524 comprising the concept set 518 is provided to a structured database query processor 420 within a query service 400. In embodiments, the structured database query processor 420 may use the concept query result 524 to generate a structured database query 424 in order to extract a data record set 428 from a data repository 430.

E. Computing System Implementations

It shall be noted that the present invention may be implemented in any instruction-execution/computing device or system capable of processing data. The present invention may also be implemented into other computing devices and systems. Furthermore, aspects of the present invention may be implemented in a wide variety of ways including software, hardware, firmware, or combinations thereof. For example, the functions to practice various aspects of the present invention may be performed by components that are implemented in a wide variety of ways including discrete logic components, one or more application specific integrated circuits (ASICs), and/or program-controlled processors. It shall be noted that the manner in which these items are implemented is not critical to the present invention.

Figure 12:
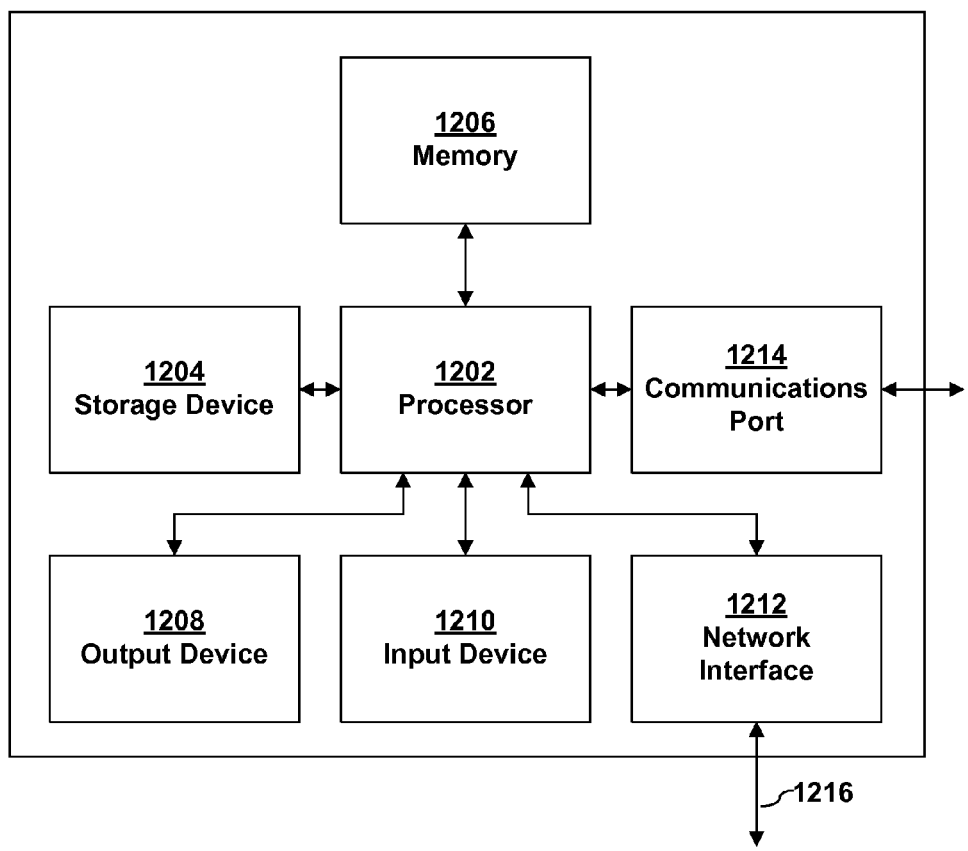
FIG. 12 depicts a block diagram of a computing system according to various embodiments of the invention.

FIG. 12 depicts a functional block diagram of an embodiment of an instruction-execution/computing device 1200 that may implement or embody embodiments of the present invention. As illustrated in FIG. 12, a processor 1202 executes software instructions and interacts with other system components. In an embodiment, processor 1202 may be a general purpose processor such as (by way of example and not limitation) an AMD processor, an INTEL processor, a SUN MICROSYSTEMS processor, or a POWERPC compatible-CPU, or the processor may be an application specific processor or processors. A storage device 1204, coupled to processor 1202, provides long-term storage of data and software programs. Storage device 1204 may be a hard disk drive and/or another device capable of storing data, such as a magnetic or optical media (e.g., diskettes, tapes, compact disk, DVD, and the like) drive or a solid-state memory device. Storage device 1204 may hold programs, instructions, and/or data for use with processor 1202. In an embodiment, programs or instructions stored on or loaded from storage device 1204 may be loaded into memory 1206 and executed by processor 1202. In an embodiment, storage device 1204 holds programs or instructions for implementing an operating system on processor 1202. In one embodiment, possible operating systems include, but are not limited to, UNIX, AIX, LINUX, Microsoft Windows, and the Apple MAC OS. In embodiments, the operating system executes on, and controls the operation of, the computing system 1200.

An addressable memory 1206, coupled to processor 1202, may be used to store data and software instructions to be executed by processor 1202. Memory 1206 may be, for example, firmware, read only memory (ROM), flash memory, non-volatile random access memory (NVRAM), random access memory (RAM), or any combination thereof. In one embodiment, memory 1206 stores a number of software objects, otherwise known as services, utilities, components, or modules. One skilled in the art will also recognize that storage 1204 and memory 1206 may be the same items and function in both capacities. In an embodiment, one or more of the components of FIGS. 4, 5, and 9 may be modules stored in memory 1204, 1206 and executed by processor 1202.

In an embodiment, computing system 1200 provides the ability to communicate with other devices, other networks, or both. Computing system 1200 may include one or more network interfaces or adapters 1212, 1214 to communicatively couple computing system 1200 to other networks and devices. For example, computing system 1200 may include a network interface 1212, a communications port 1214, or both, each of which are communicatively coupled to processor 1202, and which may be used to couple computing system 1200 to other computer systems, networks, and devices.

In an embodiment, computing system 1200 may include one or more output devices 1208, coupled to processor 1202, to facilitate displaying graphics and text. Output devices 1208 may include, but are not limited to, a display, LCD screen, CRT monitor, printer, touch screen, or other device for displaying information. Computing system 1200 may also include a graphics adapter (not shown) to assist in displaying information or images on output device 1208.

One or more input devices 1210, coupled to processor 1202, may be used to facilitate user input. Input device 1210 may include, but are not limited to, a pointing device, such as a mouse, trackball, or touchpad, and may also include a keyboard or keypad to input data or instructions into computing system 1200.

In an embodiment, computing system 1200 may receive input, whether through communications port 1214, network interface 1212, stored data in memory 1204/1206, or through an input device 1210, from a scanner, copier, facsimile machine, or other computing device.

In embodiments, computing system 1200 may include one or more databases, some of which may store data used and/or generated by programs or applications. In embodiments, one or more databases may be located on one or more storage devices 1204 resident within a computing system 1200. In alternate embodiments, one or more databases may be remote (i.e. not local to the computing system 1200) and share a network 1216 connection with the computing system 1200 via its network interface 1214. In various embodiments, a database may be a relational database, such as an Oracle database, that is adapted to store, update, and retrieve data in response to SQL-formatted commands.

One skilled in the art will recognize no computing system is critical to the practice of the present invention. One skilled in the art will also recognize that a number of the elements described above may be physically and/or functionally separated into sub-modules or combined together.

It shall be noted that embodiments of the present invention may further relate to computer products with a computer-readable medium that have computer code thereon for performing various computer-implemented operations. The media and computer code may be those specially designed and constructed for the purposes of the present invention, or they may be of the kind known or available to those having skill in the relevant arts. Examples of computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present invention may be implemented in whole or in part as machine-executable instructions that may be in program modules that are executed by a computer. Examples of program modules include libraries, programs, routines, objects, components, and data structures. In distributed computing environments, program modules may be physically located in settings that are local, remote, or both.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A computer program product comprising at least one non-transitory computer-readable storage medium storing one or more sequences of instructions, wherein execution of the one or more sequences of instructions by one or more processors causes the one or more processors to generate a query to retrieve a set of stored data records from a data store by performing steps comprising:

provide a repository of terminology content, wherein the terminology content includes a plurality of backbone classes that form data structures representing a plurality of high level concepts, wherein the plurality of high level concepts includes a plurality of semantically equivalent concepts stored in one or more of domains of concepts, and wherein the plurality of semantically equivalent concepts are mapped to one another using inter-domain or intra-domain mappings defined in the terminology content;

receiving an initial query comprising a set of search criteria comprising a seed concept;

generating an equivalence concept query based on at least a subset of the search criteria that includes the seed concept;

providing the equivalence concept query to a terminology service which manages the repository of terminology content, wherein the terminology service operates to extract, from the terminology content, a set of concepts that are semantically equivalent to the seed concept using the defined mappings;

receiving the set of concepts that are semantically equivalent to the seed concept in response to submitting the equivalence concept query to the terminology service; and generating a structured query language (SQL) query for retrieving a set of structured records from an electronic data record system, wherein the SQL query comprises predicates corresponding to the seed concept and the set of concepts semantically equivalent to the seed concept, and an equality predicate that compares a search criterion attribute value to a value within a structured record to determine they are equal.

2. The computer program product of claim 1 wherein the terminology content comprises concepts that are associated with at least one terminology code system.

3. The computer program product of claim 2 wherein the seed concept has a coded data type.

4. The computer program product of claim 1 wherein the subset of search criteria comprises an equivalence definition type.

5. The computer program product of claim 4 wherein the equivalence definition type is semantic equivalence or mapping equivalence.

6. The computer program product of claim 2 wherein the subset of search criteria comprises an indication of an equivalence definition domain boundary.

7. The computer program product of claim 6 wherein the equivalence definition domain boundary is indicated to be within a single code system associated with a terminology or is indicated to span across a plurality of code systems associated with a plurality of terminologies.

8. The computer program product of claim 6 wherein the equivalence definition domain boundary is indicated to be within a usage context.

9. A system to generate a database query to retrieve a set of stored data records from a data store, the system comprising:

a computer including memory and one or more microprocessors;

a concept query system that executes on the computer, wherein the concept query system operates to receive a query comprising a set of search criteria that comprises a seed concept, generate an equivalence concept query based on at least a subset of the search criteria that includes the seed concept, provide the equivalence concept query to a terminology service that manages a repository of terminology content, wherein the terminology content includes a plurality of backbone classes that form data structures representing a plurality of high level concepts, wherein the plurality of high level concepts includes a plurality of semantically equivalent concepts stored in one or more of domains of concepts, and wherein the plurality of semantically equivalent concepts are mapped to one another using inter-domain or intra-domain mappings defined in the terminology content, wherein the terminology service operates to extract, from the terminology content, a set of concepts that are semantically equivalent to the seed concept using the defined mappings, and receive a concept query result comprising the seed concept and an extracted set of concepts that are semantically equivalent to the seed concept; and a database query generator to receive the concept query result and generate a structured query language (SQL) query for retrieving a set of structured records from a database, where the SQL query comprises predicates associated with the seed concept and the retrieved set of concepts semantically equivalent to the seed concept, and an equality predicate that compares a search criterion attribute value to a value within a structured record to determine they are equal.

10. The system of claim 9 further comprising a database query processor to receive the database query and retrieve the set of stored data records in response to submitting the database query to the data store.

11. The system of claim 9 wherein the terminology content comprises stored concepts that are associated with at least one terminology code system.

12. The system of claim 11 wherein the seed concept has a coded data type.

13. The system of claim 12 wherein the subset of search criteria comprises an equivalence definition type.

14. The system of claim 13 wherein the equivalence definition type is semantic equivalence or mapping equivalence.

15. A computer implemented method for generating a set of semantically equivalent concepts for generating a database query for retrieving a set of stored data records from an electronic data record system, the method comprising:

providing a repository of terminology content, wherein the terminology content includes a plurality of backbone classes that form data structures representing a plurality of high level concepts, wherein the plurality of high level concepts includes a plurality of semantically equivalent concepts stored in one or more of domains of concepts, and wherein the plurality of semantically equivalent concepts are mapped to one another using inter-domain or intra-domain mappings defined in the terminology content;

receiving an initial query comprising a set of search criteria comprising a seed concept;

generating an equivalence concept query based on at least a subset of the search criteria that includes the seed concept;

providing the equivalence concept query to a terminology service which manages the repository of terminology content, wherein the terminology service operates to extract, from the terminology content, a set of concepts that are semantically equivalent to the seed concept using the defined mappings;

receiving the set of concepts that are semantically equivalent to the seed concept in response to submitting the equivalence concept query to the terminology service; and generating a structured query language (SQL) query for retrieving a set of structured records from an electronic data record system, wherein the SQL query comprises predicates corresponding to the seed concept and the set of concepts semantically equivalent to the seed concept, and an equality predicate that compares a search criterion attribute value to a value within a structured record to determine they are equal.

16. The method of claim 15 wherein the terminology content data repository comprises stored concepts that are associated with at least one terminology code system.

17. The method of claim 16 wherein the seed concept has a coded data type.

18. The method of claim 17 wherein the set of semantically equivalent concepts have inter-version semantic equivalence.

19. The method of claim 17 wherein the set of semantically equivalent concepts are associated with a plurality of terminology codes and have inter-terminology mapping equivalence.

* * * * *